United States Patent
Ohta et al.

(10) Patent No.: US 9,757,094 B2
(45) Date of Patent: Sep. 12, 2017

(54) ULTRASOUND DIAGNOSTIC APPARATUS, SOUND VELOCITY SETTING METHOD, AND RECORDING MEDIUM

(71) Applicant: FUJIFILM Corporation, Tokyo (JP)

(72) Inventors: Yasunori Ohta, Ashigara-kami-gun (JP); Tsuyoshi Tanabe, Ashigara-kami-gun (JP); Noriaki Ida, Ashigara-kami-gun (JP); Shin Nakata, Ashigara-kami-gun (JP); Hiroshi Yamaguchi, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 188 days.

(21) Appl. No.: 14/139,534

(22) Filed: Dec. 23, 2013

(65) Prior Publication Data

US 2014/0187952 A1    Jul. 3, 2014

(30) Foreign Application Priority Data

Dec. 27, 2012   (JP) ................. 2012-284613

(51) Int. Cl.
*A61B 6/00* (2006.01)
*A61B 8/00* (2006.01)
*A61B 8/14* (2006.01)
*A61B 8/08* (2006.01)
*G01S 7/52* (2006.01)

(52) U.S. Cl.
CPC ............... *A61B 8/585* (2013.01); *A61B 8/14* (2013.01); *A61B 8/5207* (2013.01); *A61B 8/5269* (2013.01); *A61B 8/54* (2013.01); *G01S 7/52049* (2013.01); *G01S 7/52085* (2013.01); *A61B 8/4483* (2013.01)

(58) Field of Classification Search
CPC .................. G01S 7/52046; G01S 15/8927
See application file for complete search history.

(56) References Cited

U.S. PATENT DOCUMENTS

| | | | | |
|---|---|---|---|---|
| 2003/0013955 A1* | 1/2003 | Poland | ............... | G01S 7/52069 600/437 |
| 2008/0242999 A1* | 10/2008 | Kakee | ............... | 600/458 |
| 2009/0118619 A1* | 5/2009 | Oshiki | ............... | 600/459 |
| 2011/0077519 A1 | 3/2011 | Katsuyama | | |

FOREIGN PATENT DOCUMENTS

| | | |
|---|---|---|
| EP | 0421279 A1 | 4/1991 |
| JP | 3-176040 A | 7/1991 |
| JP | 2011-92686 A | 5/2011 |
| JP | 2012-157387 A | 8/2012 |

OTHER PUBLICATIONS

Japanese Office Action for Japanese Application No. 2012-284613, dated Dec. 2, 2014, with a partial English translation.

* cited by examiner

*Primary Examiner* — Tse Chen
*Assistant Examiner* — Hien Nguyen
(74) *Attorney, Agent, or Firm* — Birch, Stewart, Kolasch & Birch, LLP

(57) ABSTRACT

An ultrasound diagnostic apparatus performs transmission and reception of ultrasonic waves for forming focal points used to set sound velocities at predetermined timing such that sound velocities having been set for all of respective segment regions established by dividing a subject are all reset every predetermined number of frames. Owing to this configuration, it becomes possible for the ultrasound diagnostic apparatus to suitably reset sound velocities of ultrasonic waves in the subject and also reduce the amount of calculation for resetting sound velocities.

9 Claims, 3 Drawing Sheets

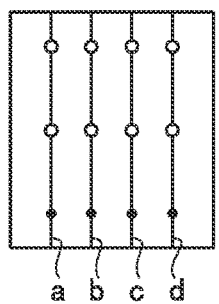
FIG.5A
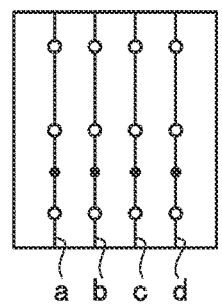
FIG.5B
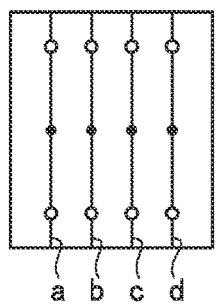
FIG.5C
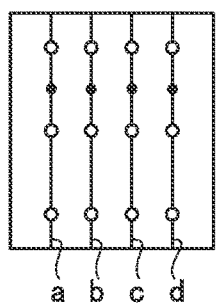
FIG.5D
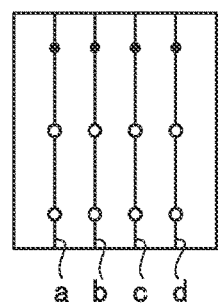
FIG.5E
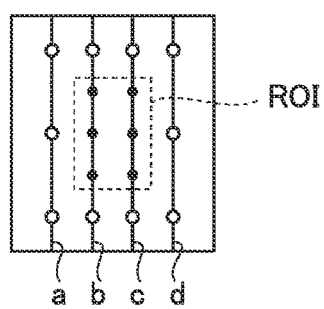
FIG.6A
FIG.6B
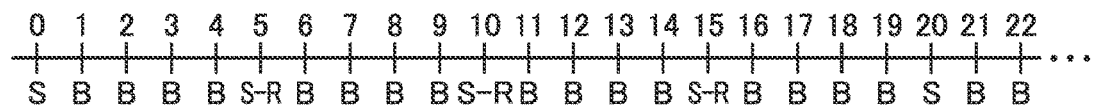

ULTRASOUND DIAGNOSTIC APPARATUS, SOUND VELOCITY SETTING METHOD, AND RECORDING MEDIUM

BACKGROUND OF THE INVENTION

The present invention relates to an ultrasound diagnostic apparatus, particularly to an ultrasound diagnostic apparatus, a sound velocity setting method, and a recording medium for setting sound velocities of ultrasonic waves in a subject.

Ultrasound diagnostic apparatuses using ultrasound images are put to practical use in the medical field.

In general, this type of ultrasound diagnostic apparatus includes an ultrasound probe (hereinafter also called "probe") having a piezoelectric element array in which piezoelectric elements transmitting and receiving ultrasonic waves are arranged, and a diagnostic apparatus body.

The ultrasound diagnostic apparatus transmits ultrasonic waves from the probe into a subject's body, receives the ultrasonic echo from the subject with the probe, and electrically processes the resulting reception signals with the diagnostic apparatus body to produce an ultrasound image.

The piezoelectric element array of the ultrasound probe receives through a plurality of piezoelectric elements an ultrasonic echo resulted from one transmission of an ultrasonic beam. Accordingly, even though an ultrasonic echo results from reflection at the same reflection point, the time taken to enter each piezoelectric element varies depending on the position of the piezoelectric element.

To cope with it, the ultrasound diagnostic apparatus performs delay correction separately on reception signals output from the ultrasound probe using a delay time corresponding to, for example, the position of each piezoelectric element, and performs matching addition with phases having been adjusted by the delay correction to produce a sound ray signal (sound ray data), thereby producing a proper ultrasound image without distortion.

The delay correction is performed with the use of the sound velocity of ultrasonic waves (hereinafter also referred to as simply "sound velocity") in the subject. In a conventional ultrasound diagnostic apparatus, the sound velocity in a subject is assumed to be constant, so that the sound velocity of ultrasonic waves is fixed to a certain set value (e.g., 1520 m/sec).

However, the sound velocity of ultrasonic waves in a subject is not constant since the sound velocity varies depending on differences in tissue property in a fat layer, a muscular layer, and the like in a living body. Specifically, the sound velocity of ultrasonic waves in a subject differs depending on the position. In addition, a fat examinee and a thin examinee differ in the thickness of a fat layer or a muscular layer.

As a result, in the case of using such a conventional ultrasound diagnostic apparatus in which the sound velocity of ultrasonic waves is fixed, an actual sound velocity in a subject and a set sound velocity are often different from each other.

When the set sound velocity is different from the actual sound velocity, it hinders accurate delay correction. Consequently, a produced ultrasound image is to, for instance, contain a distortion as compared to the actual subject, so that the image quality of the ultrasound image is degraded.

To cope with it, JP 2011-92686 A proposes an ultrasound diagnostic apparatus that sets regions of interest by dividing the inside of a subject (ultrasound image) into multiple regions, and sets a sound velocity for each of the regions of interest. Specifically, in this apparatus, transmission and reception of ultrasonic waves for forming a transmission focus point corresponding to a region of interest is performed. Reception signals obtained through this transmission and reception are set with a plurality of sound velocities and delay correction and matching addition are performed to calculate a focus index (e.g., luminance) for every region of interest at each sound velocity. From the result, the sound velocity with which the highest focus index has been obtained is set as the sound velocity of the region of interest.

According to JP 2011-92686 A, the ultrasound diagnostic apparatus can deal with the individual variability of subjects or differences among regions in a subject, which enables to set accurate sound velocities to perform delay correction. Therefore, the ultrasound diagnostic apparatus can produce a high quality ultrasound image without distortion or the like.

Furthermore, in the ultrasound diagnostic apparatus stated in JP 2011-92686 A, the inside of a subject is finely divided by, for example, defining regions of interest to be small and a sound velocity is set for each local region, whereby an ultrasound image with still higher image quality can be produced.

SUMMARY OF THE INVENTION

The sound velocity in a subject varies depending on the state of tissue of a muscle or the like. In addition, when the position of a probe is changed, the sound velocity of a subject in a region where the probe abuts is changed accordingly.

Hence, in order to consistently produce a high quality ultrasound image, it is preferred to appropriately update (reset) the sound velocity.

In an ultrasound diagnostic apparatus, setting the sound velocity needs a lot of calculations. Accordingly, the update of sound velocities is a great burden on the ultrasound diagnostic apparatus.

As described above, setting a sound velocity for each local region in a subject makes it possible to produce a high quality ultrasound image. As the size of the local regions is smaller, the image quality of the ultrasound image can be higher. However, as the size of the local regions is smaller, it increases the amount of calculation for setting sound velocities, which may cause a problem that, for instance, the calculation processing cannot keep up with the setting of sound velocities.

An object of the present invention is to solve the foregoing problem of the prior art and, as the first aspect, to provide an ultrasound diagnostic apparatus capable of suppressing the amount of calculation for setting sound velocities therein, and appropriately updating sound velocities even when setting a sound velocity for each of small local regions in a subject, thereby stably maintaining a high quality ultrasound image.

An object of the present invention is, as the second aspect, to provide a sound velocity setting method capable of suppressing the amount of calculation for setting sound velocities in the ultrasound diagnostic apparatus, and appropriately updating sound velocities even when setting a sound velocity for each of small local regions in a subject, thereby stably maintaining a high quality ultrasound image.

An object of the present invention is, as the third aspect, to provide a recording medium storing a computer program capable of suppressing the amount of calculation for setting sound velocities in the ultrasound diagnostic apparatus, and appropriately updating sound velocities even when setting a sound velocity for each of small local regions in a subject, thereby stably maintaining a high quality ultrasound image.

In order to attain the object, the present invention provides an ultrasound diagnostic apparatus comprising:

a piezoelectric element array having piezoelectric elements arranged therein, each adapted to transmit ultrasonic waves, receive ultrasonic echoes reflected by a subject, and output reception signals according to received ultrasonic waves;

a controller adapted to control transmission and reception of ultrasonic waves by the piezoelectric element array;

a storage unit adapted to store the reception signals output by the piezoelectric element array;

a sound velocity setting unit adapted to divide the subject into multiple segment regions and set a sound velocity for each of the segment regions with use of the reception signals stored in the storage unit; and an image producer adapted to produce an ultrasound image by processing the reception signals output by the piezoelectric element array or the reception signals read out from the storage unit based on the sound velocity set for each of the segment regions, wherein the controller causes the piezoelectric element array to perform transmission and reception of ultrasonic waves for forming one or more transmission focal points for sound velocity setting by the sound velocity setting unit in one frame at predetermined timing such that sound velocities set for the respective segment regions in a predetermined region are all reset every predetermined number of frames, and wherein the sound velocity setting unit sets a sound velocity of a segment region corresponding to the one transmission focal point for sound velocity setting with use of a reception signal resulting from the transmission and reception of ultrasonic waves for forming the one transmission focal point for sound velocity setting.

In the ultrasound diagnostic apparatus according to the present invention, preferably, the predetermined region is a region corresponding to a whole area of an ultrasound image to be produced, and the controller causes the piezoelectric element array to perform transmission and reception of ultrasonic waves such that the transmission focal points for sound velocity setting are formed in the predetermined number of frames to be mutually different frame by frame Preferably, the controller causes the piezoelectric element array to perform transmission and reception of ultrasonic waves at the predetermined timing such that each frame includes at least one of scanning lines of ultrasonic waves, the scanning lines being formed with all of the transmission focal points for sound velocity setting.

Preferably, the controller causes the piezoelectric element array to perform transmission and reception of ultrasonic waves so as to form the transmission focal points for sound velocity setting in mutually different predetermined patterns at the predetermined timing.

Preferably, the predetermined timing is timing corresponding to every frame.

Preferably, the ultrasound diagnostic apparatus further comprises a region-of-interest instruction input unit, wherein the predetermined region is a region of interest set by the region-of-interest instruction input unit, and wherein the controller causes the piezoelectric element array to perform transmission and reception of ultrasonic waves so as to produce a frame formed with all of the transmission focal points for sound velocity setting in the region of interest at intervals of the predetermined number of frames.

Preferably, the controller causes the piezoelectric element array to perform transmission and reception of ultrasonic waves so as to produce a frame formed with the transmission focal points for sound velocity setting corresponding to a whole area of an ultrasound image at intervals of a second predetermined number of frames greater than the predetermined number of frames.

The present invention provides a sound velocity setting method, comprising the steps of:

at a time when a sound velocity in a subject is set by an ultrasound diagnostic apparatus, dividing the subject into multiple segment regions;

performing transmission and reception of ultrasonic waves for forming one or more transmission focal points for sound velocity setting used to set sound velocities in one frame at predetermined timing such that sound velocities set for the respective segment regions in a predetermined region are all reset every predetermined number of frames; and setting a sound velocity of a segment region corresponding to the formed transmission focal point for sound velocity setting with use of a reception signal resulting from the transmission and reception of ultrasonic waves for forming the transmission focal point for sound velocity setting.

In the sound velocity setting method according to the present invention, preferably, the predetermined region is a region corresponding to a whole area of an ultrasound image to be produced, and transmission and reception of ultrasonic waves is performed such that the transmission focal points for sound velocity setting are formed in the predetermined number of frames to be mutually different frame by frame.

Preferably, assuming the predetermined region being a set region of interest, transmission and reception of ultrasonic waves is performed so as to produce a frame formed with all of the transmission focal points for sound velocity setting in the region of interest at intervals of the predetermined number of frames.

The present invention provides a recording medium having stored therein a program that is used by an ultrasound diagnostic apparatus to set a sound velocity of a subject and that causes a computer to implement:

a dividing step of dividing the subject into multiple segment regions;

a transmission and reception step of performing transmission and reception of ultrasonic waves for forming one or more transmission focal points for sound velocity setting used to set sound velocities in one frame at predetermined timing such that sound velocities set for the respective segment regions in a predetermined region are all reset every predetermined number of frames; and a calculation step of setting a sound velocity of a segment region corresponding to the formed transmission focal point for sound velocity setting with use of a reception signal resulting from the transmission and reception of ultrasonic waves for forming the transmission focal point for sound velocity setting.

In the recording medium according to the present invention, preferably, the stored program is configured such that the predetermined region is a region corresponding to a whole area of an ultrasound image to be produced, and such that the transmission and reception step performs transmission and reception of ultrasonic waves such that the transmission focal points for sound velocity setting are formed in the predetermined number of frames to be mutually different frame by frame.

Preferably, the stored program is configured such that, assuming the predetermined region being a set region of interest, the transmission and reception step performs transmission and reception of ultrasonic waves so as to produce a frame formed with all of the transmission focal points for sound velocity setting in the region of interest at intervals of the predetermined number of frames.

According to the present invention, in the ultrasound diagnostic apparatus, the amount of calculation for setting sound velocities of ultrasonic waves in a subject can be suppressed.

Therefore, according to the present invention, even when a sound velocity is set for each of small local regions in a subject for the purpose of higher image quality, the set sound velocities can be appropriately updated to stably maintain a high quality ultrasound image.

BRIEF DESCRIPTION OF DRAWINGS

FIGS. 5A to 5E are conceptual diagrams for explaining another example of sound velocity setting in the ultrasound diagnostic apparatus shown in FIG. 1.

FIGS. 6A and 6B are conceptual diagrams for explaining another example of sound velocity setting in the ultrasound diagnostic apparatus shown in FIG. 1.

DETAILED DESCRIPTION OF THE INVENTION

An ultrasound diagnostic apparatus, a sound velocity setting method, and a recording medium of the invention will be described in detail below with reference to the preferred embodiments shown in the accompanying drawings.

Figure 1:
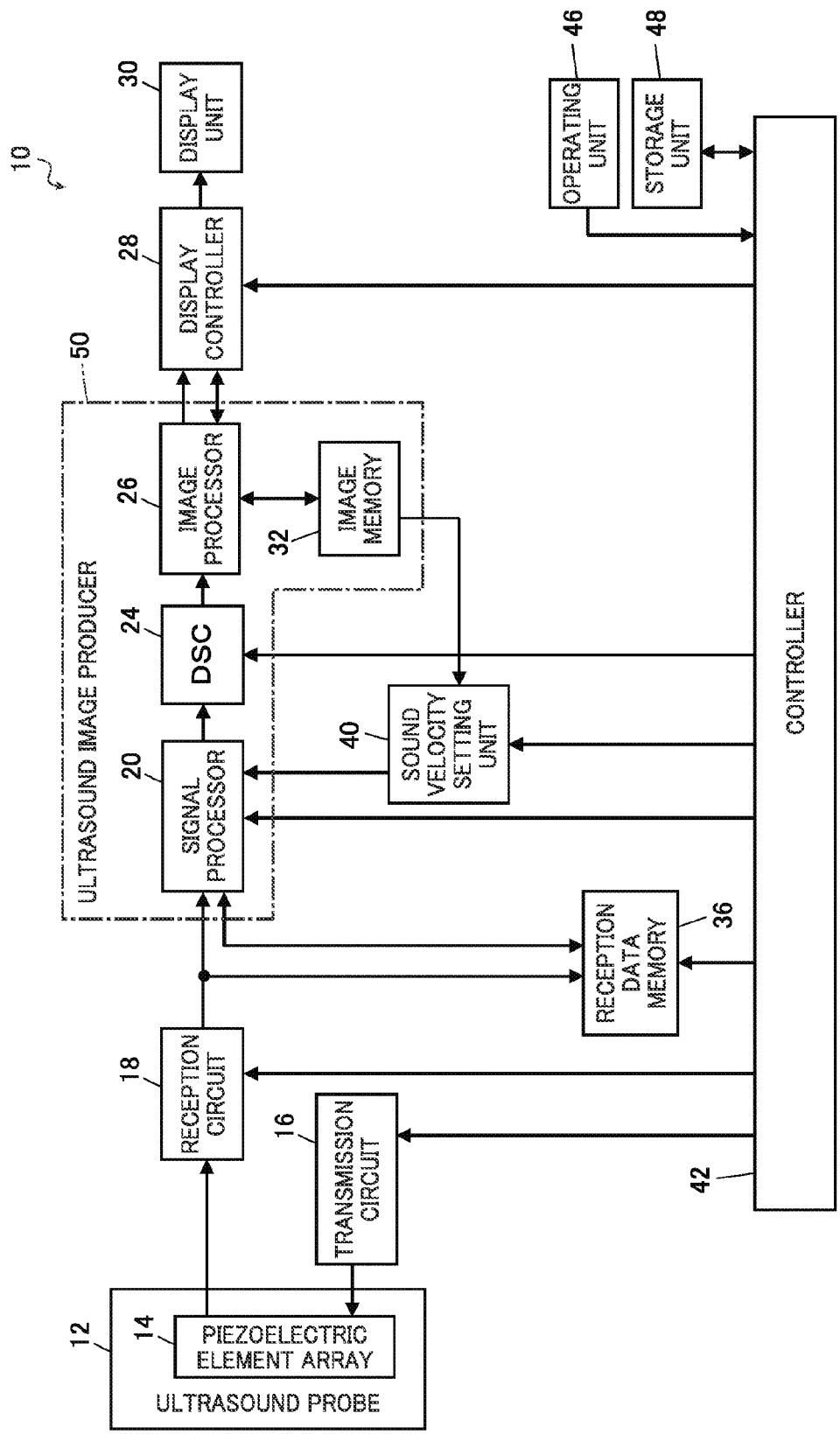
FIG. 1 is a block diagram conceptually showing an ultrasound diagnostic apparatus of the invention.

FIG. 1 is a block diagram conceptually showing an example of an ultrasound diagnostic apparatus of the invention which performs a sound velocity setting method of the invention.

As shown in FIG. 1, an ultrasound diagnostic apparatus 10 has an ultrasound probe 12 (hereinafter called "probe 12") including a piezoelectric element array 14.

The piezoelectric element array 14 of the probe 12 is connected to a transmission circuit 16 and a reception circuit 18. The reception circuit 18 is connected in sequence to a signal processor 20, a digital scan converter (DSC) 24, an image processor 26, a display controller 28, and a display unit 30. The image processor 26 is connected to an image memory 32.

The signal processor 20, the DSC 24, the image processor 26, and the image memory 32 constitute an image producer 50.

The reception circuit 18 and the signal processor 20 are connected to a reception data memory 36, and the image memory 32 and the signal processor 20 are connected to a sound velocity setting unit 40.

Furthermore, the transmission circuit 16, the reception circuit 18, the signal processor 20, the DSC 24, the display controller 28, the reception data memory 36, and the sound velocity setting unit 40 are connected to a controller 42. The controller 42 is also connected to an operating unit 46 and a storage unit 48.

In the illustrated example, the transmission circuit 16, the reception circuit 18, the ultrasound image producer 50, the display controller 28, the display unit 30, the reception data memory 36, the sound velocity setting unit 40, the controller 42, the operating unit 46, and the storage unit 48 constitute a diagnostic apparatus body of the ultrasound diagnostic apparatus 10.

The diagnostic apparatus body is constituted by, for example, a computer.

The piezoelectric element array 14 of the probe 12 includes a plurality of piezoelectric elements (ultrasound transducers) arranged one-dimensionally or two-dimensionally. These piezoelectric elements each transmit ultrasonic waves according to driving signals supplied from the transmission circuit 16 and receive ultrasonic echoes from the subject to output reception signals.

The piezoelectric element is composed of a vibrator in which electrodes are provided at the both ends of a piezoelectric body. The piezoelectric body may be composed of, for example, a piezoelectric ceramic typified by lead zirconate titanate (PZT), a piezoelectric polymer typified by polyvinylidene fluoride (PVDF), or a piezoelectric monocrystal typified by lead magnesium niobate-lead titanate solid solution (PMN-PT).

When a pulsed voltage or a continuous-wave voltage is applied to the electrodes of such a vibrator, the piezoelectric body expands and contracts to cause the vibrator to generate pulsed or continuous ultrasonic waves. These ultrasonic waves are synthesized to form an ultrasonic beam.

Upon reception of propagating ultrasonic waves, the vibrators expand and contract to produce electric signals. The electric signals are output from the piezoelectric elements of the piezoelectric element array 14 as reception signals of the ultrasonic waves.

The transmission circuit 16 includes, for instance, a plurality of pulse generators. The transmission circuit 16 adjusts delay amounts of the driving signals and then supplies the adjusted driving signals to the respective piezoelectric elements so that the ultrasonic waves transmitted from the piezoelectric element array 14 form an ultrasonic beam as desired. The transmission circuit 16 adjusts each delay amount based on a transmission delay pattern selected in accordance with a control signal from the controller 42.

The reception circuit 18 amplifies the reception signals transmitted from the piezoelectric elements of the piezoelectric element array 14 and analog-to-digital converts the amplified signals to produce pieces of digitalized reception data as many as the number of reception channels.

At this time, in response to an instruction sent from the controller 42, the transmission circuit 16 and the reception circuit 18 cause the piezoelectric element array 14 to perform transmission and reception of ultrasonic waves for forming transmission focal points to be used by the sound velocity setting unit 40 to set sound velocities of ultrasonic waves in the subject (transmission focal points for sound velocity setting) at predetermined timing as appropriately set, for instance, for every frame, once in every two frames, once in every five frames, once in every ten frames, once in every twenty frames, and so forth.

Hence, in the ultrasound diagnostic apparatus 10, sound velocities set for respective segment regions in a predetermined region in the subject are all updated by transmission and reception of ultrasonic waves for a predetermined number of frames.

This point will be described in detail later.

The signal processor 20 implements delay correction on each piece of reception data produced by the reception circuit 18 based on a sound velocity (a set sound velocity and an optimal sound velocity to be described below) input from the sound velocity setting unit 40, thereby producing pieces of delay correction data. Subsequently, the signal processor 20 adds the produced pieces of delay correction data (performs matching addition) to perform a reception focusing process. By this process, the ultrasonic echo is well focused so as to produce a sound ray signal (sound ray data).

Furthermore, the signal processor 20 corrects the sound ray signal for the attenuation due to distance according to the depth at which the ultrasonic waves are reflected, and then performs an envelope detection process. By this process, the signal processor 20 produces a B-mode image signal (ultrasound image) which is tomographic image information relating to the tissue in the subject.

The DSC 24 converts the B-mode image signal produced by the signal processor 20 into an image signal compatible with an ordinary television signal scanning mode (raster conversion).

The image processor 26 performs various kinds of necessary image processing such as gradation processing on the B-mode image signal entered from the DSC 24, and outputs the B-mode image signal to the display controller 28. Alternatively, the image processor 26 stores the B-mode image signal having been subjected to the necessary processing in the image memory 32.

As described above, the ultrasound image producer 50 is made up of the signal processor 20, the DSC 24, the image processor 26, and the image memory 32.

Based on the B-mode image signal having been subjected to the image processing by the image processor 26 and various kinds of information input by the operating unit 46, the display controller 28 causes the display unit 30 to display an ultrasound image and the like.

The display unit 30 includes a display device such as an LCD, for example, and displays the ultrasound image under the control of the display controller 28. In this example, the display controller 28 and the display unit 30 are capable of displaying color images.

The reception data memory 36 sequentially stores the reception data output from the reception circuit 18 and also stores the delay correction data produced by the signal processor 20.

The sound velocity setting unit 40 sets sound velocities of ultrasonic waves (optimal sound velocities to be described below) in the subject.

In the present invention, as an example, the sound velocity setting unit 40 provides a predetermined set sound velocity to the signal processor 20 and, while changing the set sound velocity, causes the ultrasound image producer 50 to produce B-mode image signals. The sound velocity setting unit 40 analyzes B-mode images thus produced with the different set sound velocities and sets a sound velocity at which the contrast or the sharpness of the image is highest as the optimal sound velocity of the subject. The sound velocity setting unit 40 also divides the inside of the subject into multiple segment regions and sets an optimal sound velocity for each of the segment regions.

The controller 42 controls components of the ultrasound diagnostic apparatus according to instructions entered by the operator using the operating unit 46.

The controller 42 also issues instructions to the transmission circuit 16 and the reception circuit 18 to cause the piezoelectric element array 14 to transmit an ultrasonic beam as desired and receive an ultrasonic echo resulting from the ultrasonic beam to output a reception signal.

The operating unit 46 is provided for the operator to perform input operations and may be composed of, for example, a keyboard, a mouse, a track ball, and/or a touch panel. The operating unit 46 includes a region-of-interest (ROI) instruction input unit (ROI setting means). The input of instructions on a region of interest may be performed by a known method employed in ultrasound diagnostic apparatuses.

The storage unit 48 stores, for example, an operation program and may be constituted by, for example, a recording medium such as a hard disk, a flexible disk, an MO, an MT, a RAM, a CD-ROM, a DVD-ROM, an SD card, a CF card, and a USB memory, or a server.

The signal processor 20, the DSC 24, the image processor 26, the display controller 28, and the sound velocity setting unit 40 are each constituted by a CPU and an operation program for causing the CPU to perform various kinds of processing, but they may be each constituted by a digital circuit.

The present invention will be explained in further detail by explaining the operation of the ultrasound diagnostic apparatus 10. A recording medium according to the present invention is a recording medium that has a program stored therein for causing a computer to implement a sound velocity setting method of the invention to be described below and is readable by a computer.

As described above, in the ultrasound diagnostic apparatus 10, the subject (ultrasound image to be produced) is divided into multiple segment regions and each segment region is set by the sound velocity setting unit 40 with an optimal sound velocity which is a sound velocity of the subject.

The optimal sound velocities set for the respective segment regions are updated (reset) at predetermined timing. Further, the sound velocities of all the segment regions in a predetermined region are updated through transmission and reception of ultrasonic waves for a predetermined number of frames.

The predetermined region is exemplified by, for instance, a region corresponding to the whole area of an ultrasound image to be produced or a region of interest.

Setting (updating) of a sound velocity is carried out by transmission and reception of ultrasonic waves for forming transmission focal points for sound velocity setting (hereinafter "transmission and reception of ultrasonic waves" is also referred to simply as "transmission and reception"). In the illustrated example, transmission and reception for sound velocity setting forms transmission focal points with higher density compared to transmission and reception for B-mode image production.

Figure 2A:
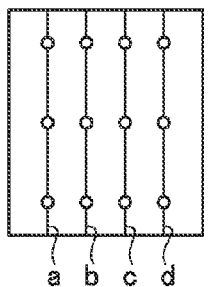
FIG. 2A is a conceptual diagram for explaining normal transmission and reception of ultrasonic waves in the ultrasound diagnostic apparatus shown in FIG. 1.

FIG. 2A conceptually shows transmission and reception for B-mode image production (hereinafter also referred to as "normal transmission and reception"), and FIG. 2B conceptually shows transmission and reception for forming transmission focal points for sound velocity setting to correspond to the whole area of an ultrasound image to be produced.

In FIG. 2, the vertical direction is the depth direction (a direction of transmission and reception of ultrasound waves), and the bottom side is a shallower side (a side closer to the piezoelectric element array 14). The horizontal direction is the azimuth direction (a direction in which the piezoelectric elements are aligned in the piezoelectric element array 14).

Figure 2B:
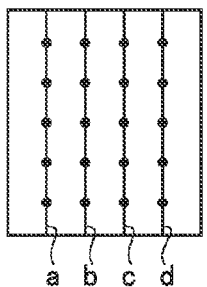
FIG. 2B is a conceptual diagram for explaining transmission and reception of ultrasonic waves for setting sound velocities in the ultrasound diagnostic apparatus shown in FIG. 1.

In FIG. 2, the solid lines extending in the depth direction represent scanning lines (sound ray signals to be produced=ultrasonic beams to be produced). The positions of the scanning lines in the azimuth direction are the same between the normal transmission and reception shown in FIG. 2A and the transmission and reception for forming focal points for sound velocity setting shown in FIG. 2B.

In FIG. 2A, white dots on the scanning lines represent transmission focal points in the normal transmission and reception. In FIG. 2B, black dots on the scanning lines represent transmission focal points for sound velocity setting (hereinafter also referred to as "focal points for setting").

It should be noted that, in the present invention, the number of scanning lines and the number of focal points are not limited to this example.

In this regard, the same applies to examples of FIGS. 3 to 6 to be described later.

In this example, as shown in FIG. 2, in the normal transmission and reception, three transmission focal points are set for one scanning line to be different in the position in the depth direction. Specifically, in the normal transmission and reception, transmission and reception is performed three times with different transmission focal points for one scanning line.

On the other hand, the number of focal points for setting to be set for one scanning line is five. Specifically, in setting optimal sound velocities, transmission and reception is performed five times with different transmission focal points for one scanning line to form all the focal points for setting.

On each scanning line, the shallowest focal point for setting, the middle-depth focal point for setting, and the deepest focal point for setting are located at the same positions as the transmission focal points of the normal transmission and reception. Thus, those three focal points each serve as both a transmission focal point of the normal transmission and reception for B-mode image production and a focal point for setting.

The segment regions each set with an optimal sound velocity are defined by dividing the subject in the azimuth direction and in the direction parallel to the depth direction to establish a grid pattern with the focal points for setting being taken as centers of the respective segment regions.

Specifically, an optimal sound velocity is set to correspond to each focal point for setting.

The segment regions of the subject, i.e., the focal points for setting to be formed may be set as appropriate in accordance with desired image quality, a frame rate of an ultrasound image to be displayed, calculation capacity (processing speed) of the ultrasound diagnostic apparatus 10, or the like.

Preferably, focal points for setting are each formed at the same position in every pixel of an ultrasound image to be produced. Alternatively, one focal point for setting may be given for several pixels whose number is appropriately determined in such a manner of giving, for example, one focal point for setting per three pixels, nine pixels, and so forth. Still alternatively, segment regions may be set by equally dividing an ultrasound image by an appropriately-set number, for example, by 10 or 20.

Furthermore, the number of segment regions (focal points for setting), the number of focal points for setting for one scanning line, or the like may be determined by the operator (doctor). The foregoing setting of focal points for setting may be made through the operation of mode selection or the like.

It should be noted that, in the present invention, a focal point for setting is not necessarily formed to correspond to every segment region. For instance, a segment region having no focal point for setting may be provided, and an optimal velocity setting may be set for this segment region by interpolation with the use of optimal sound velocities set for segment regions having focal points for setting.

As described above, in the normal transmission and reception and the transmission and reception for sound velocity setting, the number of scanning lines in one frame and the number of focal points for one scanning line are not limited to the example shown in FIG. 3. For instance, in the normal transmission and reception, one scanning line may be formed not with three transmission focal points (by three times of transmission and reception) but with one transmission focal point (by one time of transmission and reception). Specifically, in the normal transmission and reception and the transmission and reception for sound velocity setting in the present invention, it suffices if the number of transmission focal points (the number of times of transmission and reception) for one scanning line in the transmission and reception for sound velocity setting is made greater.

While, in the example shown in FIG. 3, only the number of transmission focal points for one scanning line in the transmission and reception for sound velocity setting is greater than that in the normal transmission and reception, the transmission and reception for sound velocity setting may also have more scanning lines than the normal transmission and reception, as necessary.

As described above, in the normal transmission and reception, as shown in FIG. 2A, transmission and reception of ultrasonic waves is performed three times to form three transmission focal points for one scanning line.

On the other hand, in order to set an optimal sound velocity, transmission and reception of ultrasonic waves is performed five times to form five focal points for setting for one scanning line.

In this example, the ultrasound diagnostic apparatus 10 repeatedly performs transmission and reception of ultrasonic waves as conceptually shown in FIGS. 3A to 3D to update an optimal sound velocity of each of all the segment regions (all the focal points for setting) in four frames, while producing an ultrasound image (B-mode image).

Figure 3A:
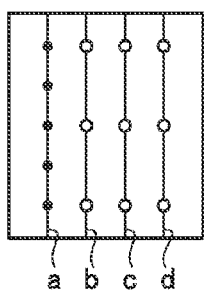
FIGS. 3A to 3D are conceptual diagrams for explaining one example of sound velocity setting in the ultrasound diagnostic apparatus shown in FIG. 1.

Specifically, in the transmission and reception shown in FIG. 3A, transmission and reception of ultrasonic waves for forming focal points for setting is performed only for a scanning line a at the leftmost (in the drawing), and the normal transmission and reception of ultrasonic waves is performed for the other scanning lines. In the transmission and reception shown in FIG. 3B, transmission and reception of ultrasonic waves for forming focal points for setting is performed only for the second left scanning line b, and the normal transmission and reception of ultrasonic waves is performed for the other scanning lines. In the transmission and reception shown in FIG. 3C, transmission and reception of ultrasonic waves for forming focal points for setting is performed only for the third left scanning line c, and the normal transmission and reception of ultrasonic waves is performed for the other scanning lines. In the transmission and reception shown in FIG. 3F, transmission and reception of ultrasonic waves for forming focal points for setting is performed only for the fourth left scanning line d, and the normal transmission and reception of ultrasonic waves is performed for the other scanning lines.

Figure 3B:
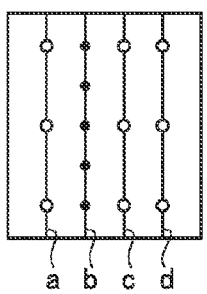
Figure 3C:
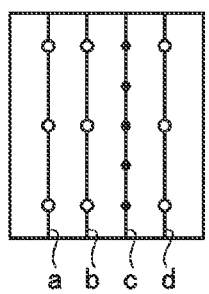
Figure 3D:
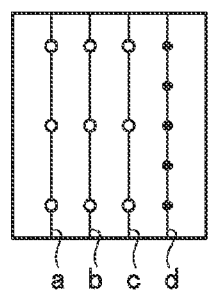

In the following, for convenience, the frame in FIG. 3A, the frame in FIG. 3B, the frame in FIG. 3C, and the frame in FIG. 3D are defined as the first frame, the second frame, the third frame, and the fourth frame, respectively.

When the ultrasound diagnostic apparatus 10 carries out a diagnosis, the transmission circuit 16 operates the piezoelectric element array 14 to transmit an ultrasonic beam for forming a desired transmission focal point. The reception circuit 18 operates the piezoelectric element array 14 to receive an ultrasonic echo resulting from the ultrasonic beam. The transmission circuit 16 and the reception circuit 18 perform the above operations in response to an instruction from the controller 42.

In the first frame shown in FIG. 3A, as described above, transmission and reception is performed to form focal points for setting on the scanning line a. Specifically, for the first frame, transmission and reception is performed five times with mutually different transmission focal points (focal points for setting) for the scanning line a, while transmission and reception is performed three times with mutually different transmission focal points for the other three scanning lines b, c and d.

Reception signals output from the respective piezoelectric elements of the piezoelectric element array 14 through the transmission and reception of ultrasonic waves for the first frame undergo amplification and A/D conversion by the reception circuit 18, and the resulting pieces of reception data are sequentially stored in the reception data memory 36.

After the pieces of reception data are stored in the reception data memory 36, the signal processor 20 reads out and subjects the pieces of reception data to delay correction based on the previously-set optimal sound velocities to produce pieces of delay data. Then the signal processor 20 adds the produced pieces of delay data to perform a reception focusing process to thereby produce a sound ray signal. The signal processor 20 further implements correction of attenuation and an envelope detection process on the sound ray signal to thereby produce a B-mode image signal.

At this time, with regard to the scanning line a for which the focal points for setting are formed in the first frame, reception data corresponding to the second deepest focal point for setting and reception data corresponding to the fourth deepest focal point for setting may be used for production of a B-mode image signal. Whether to use, in production of a B-mode image signal, reception data corresponding to a focal point for setting which is not formed in the normal transmission and reception may be appropriately determined depending on required image quality or the like.

Reception data for use in production of a B-mode image may be not read out from the reception data memory 36 but directly supplied from the reception circuit 18 to the signal processor 20.

The configuration above applies to transmission and reception of ultrasonic waves for the other frames (including examples shown in FIG. 4 and the like).

In the case where optimal sound velocities have not yet been set for the respective segment regions of a subject at the start of diagnosis or the like, a sound velocity set as default (e.g., 1520 m/sec) may be used to produce a sound ray signal.

Preferably, optimal sound velocities are first set for all segment regions, and then the transmission and reception shown in FIG. 3 is performed. Specifically, first, transmission and reception of ultrasonic waves for sound velocity setting for the whole area of an ultrasound image of the subject for forming focal points for setting in a region corresponding to the whole area, is performed as shown in FIG. 2B. Then optimal sound velocities are set for all segment regions with the use of reception signals obtained through this transmission and reception, as described below. Thus, it is preferred to first set optimal sound velocities for all segment regions and then perform the transmission and reception shown in FIG. 3.

A B-mode image signal of the first frame undergoes raster conversion by the DSC 24. The B-mode image signal having undergone the raster conversion is subjected to various image processing by the image processor 26 and stored in the image memory 32.

The B-mode image signal having been processed by the image processor 26 is sent to the display controller 28, so that a B-mode image of the first frame, information on the subject, and the like are displayed on the display unit 30.

In parallel with the foregoing production process of the B-mode image of the first frame for display, upon storage of reception data resulting from the transmission and reception for the first frame shown in FIG. 3A into the reception data memory 36, the sound velocity setting unit 40 supplies a first set sound velocity S1 to the signal processor 20.

The signal processor 20 reads out pieces of reception data associated with the scanning line a for which the focal points for setting are formed (reception data corresponding to the focal points for setting) from the reception data memory 36.

The signal processor 20 implements delay correction on the pieces of reception data associated with the scanning line a based on the supplied first set sound velocity S1 to produce pieces of delay data. Then the signal processor 20 adds the produced pieces of delay data to perform the reception focusing process to thereby produce a sound ray signal of the scanning line a. The signal processor 20 further implements the correction of attenuation and the envelope detection process on the sound ray signal to thereby produce a B-mode image signal of the scanning line a.

The B-mode image signal of the scanning line a undergoes raster conversion by the DSC 24 and then various kinds of image processing by the image processor 26 in the same manner as above. The B-mode image signal is stored in the image memory 32 as a B-mode image signal for sound velocity setting of the scanning line a.

Upon storage of the B-mode image signal corresponding to the first set sound velocity S1 supplied from the sound velocity setting unit 40 into the image memory 32, the sound velocity setting unit 40 supplies the signal processor 20 with a second set sound velocity S2 having a value changed from the first set sound velocity S1 by a predetermined amount. As a result, similarly to the forgoing, a B-mode image for sound velocity setting of the scanning line a for which the focal points for setting are formed is produced based on the second set sound velocity S2, and stored in the image memory 32.

Thus, the sound velocity setting unit 40 provides a plurality of set sound velocities S1 to Sn to the signal processor 20 in sequence, and B-mode image signals of the scanning line a corresponding to those set sound velocities S1 to Sn are produced by the ultrasound image producer 50. The B-mode image signals of the scanning line a are stored in the image memory 32 as B-mode image signals for sound velocity setting.

Upon storing in the image memory 32 the B-mode image signals corresponding to the set sound velocities S1 to Sn as set for the scanning line a for which the focal points for setting are formed, the sound velocity setting unit 40 performs the analysis on the B-mode image signals of the scanning line a and the B-mode image signal of the first frame stored in the image memory 32. Based on the results of the analysis, the sound velocity setting unit 40 sets a sound velocity at which the contrast or the sharpness of the image is highest as an optimal sound velocity of the subject with respect to the scanning line a.

The analysis on B-mode image signals and the setting of an optimal sound velocity are performed for each of the segment regions, i.e., each of the focal points for setting, of the scanning line a. Specifically, a sound velocity at which the contrast or the sharpness of the image is highest is selected for each of the segment regions of the scanning line a to be set as the optimal sound velocity of each of the segment regions of the scanning line a.

Thus, the optimal sound velocity is a sound velocity from a segment region to the piezoelectric elements, where the sound velocity is considered as constant in the subject from the segment region to the piezoelectric elements. In other words, the optimal sound velocity is an average sound velocity in the subject from a segment region to the piezoelectric elements.

The sound velocity setting unit 40 links, in place of an optimal sound velocity as previously set for the scanning line a, a newly-set optimal sound velocity to a relevant segment region and stores the same. Specifically, the sound velocities of the scanning line a are updated to the newly-set sound velocities.

A method of setting a sound velocity of a subject is not limited to the foregoing method and use may be made of various known sound velocity setting methods employed in ultrasound diagnostic apparatuses or ultrasound image production methods.

Upon completion of transmission and reception of ultrasonic waves for the first frame, then transmission and reception of ultrasonic waves for the second frame is performed as shown in FIG. 3B.

As described above, in the second frame, transmission and reception of ultrasonic waves is performed to form focal points for setting only for the scanning line b positioned at the second end from the left in the drawing. Specifically, for the second frame, transmission and reception of ultrasonic waves is performed five times with mutually different focal points for setting only for the scanning line b, while transmission and reception of ultrasonic waves is performed three times with mutually different transmission focal points for the other three scanning lines a, c and d.

Similarly to the foregoing, reception signals obtained through transmission and reception of ultrasonic waves for the second frame undergo amplification and A/D conversion by the reception circuit 18, and the resulting pieces of reception data are stored in the reception data memory 36.

Upon storage of the pieces of reception data into the reception data memory 36, the signal processor 20 reads out the pieces of reception data, and implements delay correction on the pieces of reception data based on optimal sound velocities as previously set and stored in the sound velocity setting unit 40 to perform the reception focusing process to thereby produce a sound ray signal. Accordingly, for the scanning line a, the optimal sound velocities as updated by the foregoing transmission and reception for the first frame are used to implement delay correction to produce a sound ray signal.

The signal processor 20 further implements the correction of attenuation and the envelope detection process on the sound ray signal to thereby produce a B-mode image signal.

There may be cases where the update of the optimal sound velocities of the scanning line a performed for the first frame is not completed before the delay correction for the second frame. In this case, the optimal sound velocities updated for the first frame may be used to process reception data obtained through transmission and reception for the subsequent frames following the processing for the second frame. In this regard, the same applies to reception data obtained through transmission and reception for all the frames.

The produced B-mode image signal undergoes raster conversion by the DSC 24 and then image processing by the image processor 26, and subsequently, is stored in the image memory 32 as a B-mode image signal of the second frame. The display controller 28 causes the display unit 30 to display the produced B-mode image signal.

In parallel with the foregoing process of producing the B-mode image for display of the second frame, upon storage of reception data resulting from the transmission and reception for the second frame shown in FIG. 3B into the reception data memory 36, the signal processor 20 reads out reception data associated with the scanning line b for which the focal points for setting are formed (reception data corresponding to the focal points for setting) from the reception data memory 36. The sound velocity setting unit 40 supplies the set sound velocities S1 to Sn to the signal processor 20.

Similarly to the foregoing, based on the set sound velocities S1 to Sn, the signal processor 20 performs the same processing as above on the read-out reception data associated with the scanning line b to produce B-mode image signals. The produced B-mode image signals undergo raster conversion by the DSC 24 and then image processing by the image processor 26, and are stored in the image memory 32 as B-mode image signals for sound velocity setting of the scanning line b.

With regard to the scanning line b for which the focal points for setting are formed, upon storage of B-mode image signals for sound velocity setting corresponding to all the set sound velocities S1 to Sn into the image memory 32, the sound velocity setting unit 40 performs the image analysis in the same manner as above. Based on the results of the analysis, the sound velocity setting unit 40 sets a sound velocity at which the contrast or the sharpness of the image is highest as an optimal sound velocity of the subject in each of the segment regions (the focal points for setting) of the scanning line b.

The sound velocity setting unit 40 links, in place of an optimal sound velocity as previously set for the scanning line b, a newly-set optimal sound velocity to a relevant segment region and stores the same. Specifically, the sound velocities of the scanning line b are updated to the newly-set sound velocities.

Upon completion of transmission and reception for the second frame, then transmission and reception of ultrasonic waves for the third frame is performed as shown in FIG. 3C.

As described above, in the third frame, transmission and reception of ultrasonic waves is performed to form focal points for setting only for the scanning line c positioned at the third end from the left in the drawing. Specifically, for the third frame, transmission and reception of ultrasonic waves is performed five times with mutually different focal points for setting for the scanning line c, while transmission and reception of ultrasonic waves is performed three times with mutually different transmission focal points for the other three scanning lines a, b and d.

Similarly to the foregoing, reception signals obtained through the transmission and reception of ultrasonic waves for the third frame undergo amplification and A/D conversion by the reception circuit 18, and the resulting reception data is stored in the reception data memory 36.

Upon storage of the reception data into the reception data memory 36, the signal processor 20 reads out the reception data to be subjected to the reception focusing process, the correction of attenuation, and the envelope detection process to thereby produce a B-mode image signal in the same manner as above. In the reception focusing process, sound velocities previously updated by the transmission and reception for the first frame and the second frame are used to perform delay correction with respect to the scanning lines a and b.

The produced B-mode image signal is processed by the DSC 24 and the image processor 26, and the resulting B-mode image of the third frame is stored in the image memory 32 and displayed on the display unit 30.

In parallel with the foregoing process of producing the B-mode image for display of the third frame, upon storage of reception data resulting from the transmission and reception for the third frame shown in FIG. 3C into the reception data memory 36, the signal processor 20 reads out the reception data associated with the scanning line c for which the focal points for setting are formed (reception data corresponding to the focal points for setting) from the reception data memory 36. The sound velocity setting unit 40 supplies the set sound velocities S1 to Sn to the signal processor 20.

The signal processor 20 performs the same processing as above on the read-out reception data associated with the scanning line c to produce B-mode image signals for sound velocity setting of the scanning line c based on the set sound velocities S1 to Sn. The produced B-mode image signals are processed by the DSC 24 and the image processor 26, and are stored in the image memory 32 as B-mode image signals for sound velocity setting of the scanning line c.

The sound velocity setting unit 40 performs the analysis on the B-mode image signals for sound velocity setting stored in the image memory 32 in the same manner as above, so as to set an optimal sound velocity for each of the segment regions of the scanning line c in the subject.

The sound velocity setting unit 40 links, in place of an optimal sound velocity as previously set for the scanning line c, a newly-set optimal sound velocity to a relevant segment region and stores the same. Specifically, the sound velocities of the scanning line c are updated to the newly-set sound velocities.

Upon completion of transmission and reception for the third frame, then transmission and reception of ultrasonic waves for the fourth frame is performed as shown in FIG. 3D.

As described above, in the fourth frame, transmission and reception of ultrasonic waves is performed to form focal points for setting only for the scanning line d positioned at the fourth end from the left in the drawing. Specifically, for the fourth frame, transmission and reception of ultrasonic waves is performed five times with mutually different focal points for setting for the scanning line d, while transmission and reception of ultrasonic waves is performed three times with mutually different transmission focal points for the other three scanning lines a, b and c.

Similarly to the foregoing, reception signals obtained through the transmission and reception of ultrasonic waves for the fourth frame undergo amplification and A/D conversion by the reception circuit 18, and the resulting reception data is stored in the reception data memory 36.

Upon storage of the reception data into the reception data memory 36, the signal processor 20 reads out the reception data to produce a B-mode image signal in the same manner as above. In the reception focusing process, sound velocities previously updated by the transmission and reception for the first to third frames are used to perform delay correction with respect to the scanning lines a to c.

The produced B-mode image signal is processed by the DSC 24 and the image processor 26, and the resulting B-mode image of the fourth frame is stored in the image memory 32 and displayed on the display unit 30.

In parallel with the foregoing process of producing the B-mode image for display of the fourth frame, upon storage of reception data resulting from the transmission and reception for the fourth frame shown in FIG. 3D into the reception data memory 36, the signal processor 20 reads out the reception data associated with the scanning line d for which the focal points for setting are formed (reception data corresponding to the focal points for setting) from the reception data memory 36, and the sound velocity setting unit 40 sequentially supplies the set sound velocities S1 to Sn to the signal processor 20.

Then, in the same manner as above, the B-mode image signals for sound velocity setting are produced and subjected to the image analysis, and the sound velocity setting unit 40 sets an optimal sound velocity for each of the segment regions of the scanning line d in the subject.

The sound velocity setting unit 40 links, in place of an optimal sound velocity as previously set for the scanning line d, a newly-set optimal sound velocity to a relevant segment region and stores the same. Specifically, the sound velocities of the scanning line d are updated to the newly-set sound velocities.

Thus, in the example shown in FIG. 3, the predetermined number of frames are four frames, and optimal sound velocities of all the segment regions in the predetermined region (in this example, the whole area of an ultrasound image) are updated every four frames.

Upon completion of transmission and reception for the fourth frame, then transmission and reception of ultrasonic waves for the first frame is again performed as shown in FIG. 3A. After that, transmission and reception of ultrasonic waves shown in FIGS. 3A to 3D is repeatedly performed to produce and display B-mode image signals, and in parallel thereto, the update of optimal sound velocities for the respective scanning lines is repeatedly performed, in the above-described manner.

As described above, according to the present invention, in the ultrasound diagnostic apparatus, sound velocities (optimal sound velocities) of the respective segment regions are not all updated at a time but sequentially updated for each of the scanning lines, whereby the amount of calculation for updating (setting) sound velocities can be greatly reduced. Furthermore, since sound velocities of all the segment regions in the predetermined region are updated every predetermined number of frames, it becomes possible to prevent the image degradation such as a distortion which may be caused by an inappropriate sound velocity.

Therefore, according to the present invention, even when a sound velocity is set for each of small segment regions (local regions) in a subject for the purpose of higher image quality, sound velocities of the respective segment regions can be appropriately updated to stably maintain a high quality ultrasound image.

In the example shown in FIG. 3, transmission and reception for forming focal points for setting is performed for each scanning line and for each frame sequentially, and with respect to the scanning line for which the focal points for setting are formed, optimal sound velocities of segment regions corresponding to the focal points for setting are updated.

However, according to the present invention, optimal sound velocities of the respective segment regions may be updated in various orders other than that in the foregoing example to update sound velocities of all the segment regions in the predetermined region by the processing for a predetermined number of frames.

As an example, as shown in FIG. 4, one method is given in which sound velocities of respective segment regions are sequentially updated in a predetermined pattern set in advance.

Figure 4A:
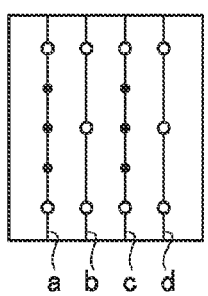
FIGS. 4A to 4D are conceptual diagrams for explaining another example of sound velocity setting in the ultrasound diagnostic apparatus shown in FIG. 1.

It is assumed that the normal transmission and reception and the focal points for setting (segment regions) are configured as the same as the foregoing example of FIG. 2. In this example, for the first frame, as shown in FIG. 4A, transmission and reception is performed to form, in addition to transmission focal points of the normal transmission and reception, the second deepest to fourth deepest focal points for setting on the scanning lines a and c to update set sound velocities of segment regions corresponding to the focal points for setting.

Thus, in the first frame, the focal points positioned in the middle in the depth direction on the scanning lines a and c each serve as both a transmission focal point of the normal transmission and reception and a focal point for setting.

Figure 4B:
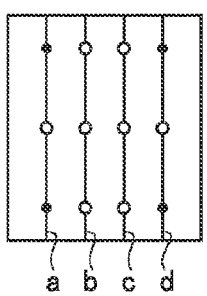

For the second frame, as shown in FIG. 4B, the normal transmission and reception is performed in the same manner as in FIG. 2A, and the shallowest focal points and the deepest focal points on the scanning lines a and d are set as focal points for setting to update set sound velocities of segment regions corresponding to the focal points for setting.

Thus, in the second frame, the shallowest focal points and the deepest focal points on the scanning lines a and d each serve as both a transmission focal point of the normal transmission and reception and a focal point for setting.

Figure 4C:
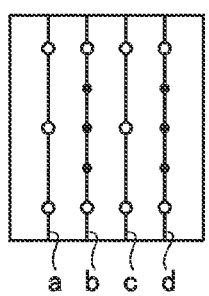

For the third frame, as shown in FIG. 4C, transmission and reception is performed to form, in addition to transmission focal points of the normal transmission and reception, the second deepest to fourth deepest focal points for setting on the scanning lines b and d to update set sound velocities of segment regions corresponding to the focal points for setting.

Thus, in the third frame, the focal points positioned in the middle in the depth direction on the scanning lines b and d each serve as both a transmission focal point of the normal transmission and reception and a focal point for setting.

Figure 4D:
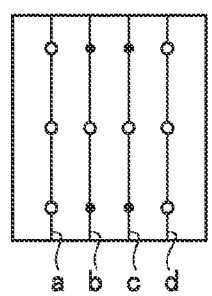

For the fourth frame, as shown in FIG. 4D, the normal transmission and reception is performed in the same manner as in FIG. 2A, and the shallowest focal points and the deepest focal points on the scanning lines b and c are set as focal points for setting to update set sound velocities of segment regions corresponding to the focal points for setting. Thus, in the fourth frame, the shallowest focal points and the deepest focal points on the scanning lines b and c each serve as both a transmission focal point of the normal transmission and reception and a focal point for setting.

Also in this example, the predetermined number of frames are four frames, and sound velocities of all the segment regions in the predetermined region (in this example, the whole area of an ultrasound image) are updated by the processing for the four frames.

As an alternative embodiment, an exemplary method of updating sound velocities in the depth order sequentially is given as shown in FIG. 5.

Similarly, it is assumed that the normal transmission and reception and the focal points for setting (segment regions) are configured as the same as the foregoing example of FIG. 2. In this example, for the first frame, as shown in FIG. 5A, the normal transmission and reception is performed in the same manner as in FIG. 2A, and the shallowest focal points on all the scanning lines are set as focal points for setting to update set sound velocities of segment regions corresponding to the focal points for setting. Thus, in the first frame, the shallowest focal points on all the scanning lines each serve as both a transmission focal point of the normal transmission and reception and a focal point for setting.

For the second frame, as shown in FIG. 5B, transmission and reception is performed to form, in addition to transmission focal points of the normal transmission and reception, the second shallowest focal points for setting on all the scanning lines to update set sound velocities of segment regions corresponding to the focal points for setting.

Also for the third frame, as shown in FIG. 5C, the normal transmission and reception is performed in the same manner as in FIG. 2A, and the focal points positioned in the middle in the depth direction on all the scanning lines are set as focal points for setting to update set sound velocities of segment regions corresponding to the focal points for setting. Thus, in the third frame, the middle-depth focal points on all the scanning lines each serve as both a transmission focal point of the normal transmission and reception and a focal point for setting.

For the fourth frame, as shown in FIG. 5D, transmission and reception is performed to form, in addition to transmission focal points of the normal transmission and reception, the fourth shallowest focal points for setting on all the scanning lines to update set sound velocities of segment regions corresponding to the focal points for setting.

Also for the fifth frame, as shown in FIG. 5E, the normal transmission and reception is performed in the same manner as in FIG. 2A, and the deepest focal points on all the scanning lines are set as focal points for setting to update set sound velocities of segment regions corresponding to the focal points for setting. Thus, in the fifth frame, the deepest focal points on all the scanning lines each serve as both a transmission focal point of the normal transmission and reception and a focal point for setting.

In this example, the predetermined number of frames are five frames, and sound velocities of all the segment regions in the predetermined region (in this example, the whole area of an ultrasound image) are updated by the processing for the five frames.

While the examples shown in FIGS. 3 to 5 are configured to form focal points for setting in every frame to update sound velocities of the respective segment regions, the present invention is not limited thereto.

For instance, transmission and reception for forming focal points for setting and the normal transmission and reception may be alternately performed frame by frame. Alternatively, transmission and reception for forming focal points for setting may be performed at intervals of an appropriately-set predetermined number of frames.

An alternative embodiment of the invention is conceptually shown in FIG. 6.

In the examples shown in FIGS. 2 to 5, a region corresponding to the whole area of an ultrasound image is assumed as the predetermined region, and sound velocities of the respective segment regions in the predetermined region are sequentially updated.

On the other hand, in the example shown in FIG. 6, assuming a region set by the operator, for instance, a region of interest (ROI) of the inside of a subject, as a predetermined region, optimal sound velocities of all segment regions in the ROI are updated at intervals of an appropriately-set predetermined number of frames.

Preferably, optimal sound velocities of segment regions of the subject covering the whole area of an ultrasound image are updated at intervals of the number of frames greater than the number of frames used for updating the optimal sound velocities of the segment regions in the ROI.

Similarly to the above, it is assumed that the normal transmission and reception and the focal points for setting are configured as the same as the foregoing example of FIG. 2, and as an example, a region indicated by the dashed line in FIG. 6A is set as the ROI.

In addition, as an example, as shown in FIG. 6B, optimal sound velocities of all segment regions in the ROI being the predetermined region are updated every five frames, while optimal sound velocities of all segment regions in the whole area of an ultrasound image are updated every twenty frames. In FIG. 6B, a frame at which the normal transmission and reception is performed is assigned "B," a frame at which optimal sound velocities in the ROI are updated "S-R," and a frame at which optimal sound velocities in the whole area of an image are updated "S."

In this embodiment, as a preferred embodiment, upon setting the ROI, transmission and reception for forming all the focal points for setting shown in FIG. 2B is performed at the beginning (for the zeroth frame) to set (update) optimal sound velocities of all the segment regions. Note that reception data resulting from this transmission and reception may be used to produce a B-mode image signal as necessary (the same applies to the twentieth frame).

Next, as shown in FIG. 6B, the normal transmission and reception shown in FIG. 2A (the transmission and reception for producing a normal B-mode image ("B")) is performed for the first to fourth frames. For the subsequent fifth frame, in addition to transmission focal points set by the normal transmission and reception, transmission and reception for forming the second deepest to fourth deepest focal points for setting on the scanning lines b and c corresponding to the ROI ("S-R") is performed as shown in FIG. 6A.

In the frames up to the fifth frame, delay correction is performed for all the segment regions based on the optimal sound velocities set for the zeroth frame to produce a B-mode image signal.

After the transmission and reception for the fifth frame is finished, optimal sound velocities are set for the segment regions (focal points for setting) in the ROI in the same manner as above to update the optimal sound velocities of the segment regions in the ROI.

Next, as shown in FIG. 6B, the normal transmission and reception shown in FIG. 2A ("B") is performed for the sixth to ninth frames. For the subsequent tenth frame, in addition to transmission focal points set by the normal transmission and reception, transmission and reception for forming the second deepest to fourth deepest focal points for setting on the scanning lines b and c corresponding to the ROI ("S-R") is performed as shown in FIG. 6A.

In the sixth to tenth frames, delay correction is performed for the segment regions in the ROI based on the optimal sound velocities updated in relation to the fifth frame and for the segment regions other than those in the ROI based on the optimal sound velocities set in relation to the zeroth frame, to produce a B-mode image signal.

After the transmission and reception for the tenth frame is finished, optimal sound velocities are set for the segment regions in the ROI in the same manner as above to update the optimal sound velocities of the segment regions in the ROI.

In the following processing up to the nineteenth frame, the normal transmission and reception (for the eleventh to fourteenth frames and the sixteenth to nineteenth frames), the update of optimal sound velocities of the segment regions in the ROI (for the fifteenth frame), and the production of a B-mode image signal are performed in the same manner. For the subsequent twentieth frame, transmission and reception for forming all the focal points for setting shown in FIG. 2B ("S") is performed to update the optimal sound velocities of all the segment regions. In the processing for the twenty-first and subsequent frames, the same processing as in the first to twentieth frames is repeatedly performed.

In this example, since optimal sound velocities are updated only for the segment regions in the ROI at intervals of a predetermined number of frames, the amount of calculation for updating sound velocities can be reduced. With regard to the ROI which is required to be intensively observed, the associated optimal sound velocities are regularly updated so that the ROI can have the higher image quality. Optimal sound velocities for the whole area of an ultrasound image are preferably also updated at intervals of the number of frames greater than that for the ROI, so that an ultrasound image giving no uncomfortable feeling can be produced.

Therefore, according to the present invention, even when a sound velocity is set for each of small segment regions in a subject for the purpose of higher image quality, the sound velocities can be appropriately updated to stably maintain a high quality ultrasound image.

It should be noted that, in the present invention, the predetermined number of frames used for updating sound velocities of all segment regions in the predetermined region may be, for instance, ten instead of four or five applied in the illustrated examples, and a variety of appropriately-set numbers are applicable.

Specifically, the predetermined number of frames used for updating sound velocities of all segment regions in the predetermined region may be appropriately determined in accordance with required image quality, a required frame rate of an ultrasound image for display, calculation capacity of the ultrasound diagnostic apparatus 10, or the like.

While the ultrasound diagnostic apparatus, the sound velocity setting method, and the recording medium of the invention have been described above in detail, the invention is by no means limited to the above embodiments, and various improvements and modifications may be made without departing from the scope and spirit of the invention.

For example, in the present invention, when sound velocities are set, not only the number of transmission focal points on one scanning line may be increased but, as necessary, the number of scanning lines may also be increased as compared to that in transmission and reception for producing a normal B-mode image.

Furthermore, in the configuration in which sound velocities of all segment regions in the ROI are updated at intervals of the predetermined number of frames as shown in FIG. 6, the respective segment regions may be sequentially updated as shown in FIGS. 3 to 5.

What is claimed is:

1. An ultrasound diagnostic apparatus comprising:
a piezoelectric element array having piezoelectric elements arranged therein, each adapted to transmit ultrasonic waves, receive ultrasonic echoes reflected by a subject, and output reception signals according to received ultrasonic waves;
a control processor adapted to control transmission and reception of ultrasonic waves by the piezoelectric element array;
a storage unit adapted to store the reception signals output by the piezoelectric element array;
a sound velocity setting processor adapted to divide the subject into multiple segment regions and set a sound velocity for each of the segment regions with use of the reception signals stored in the storage unit; and
an image producing processor adapted to produce an ultrasound image by processing the reception signals output by the piezoelectric element array or the reception signals read out from the storage unit based on the sound velocity set for each of the segment regions,
wherein the control processor causes the piezoelectric element array to perform transmission and reception of ultrasonic waves for forming transmission focal points for sound velocity setting by the sound velocity setting processor in a predetermined number of frames so as to be mutually different frame by frame and to include one of plurality of scanning lines of ultrasonic waves as a scanning line for sound velocity setting in each frame at predetermined timing such that sound velocities set for the respective segment regions in a predetermined region are all reset every predetermined number of frames, the scanning lines being formed with all of the transmission focal points for sound velocity setting,
wherein the control processor causes the piezoelectric element array to perform transmission and reception of ultrasonic waves at predetermined timing such that scanning lines excepting the one of plurality of scanning lines in each frame are the normal scanning lines of the ultrasonic waves formed of the transmission focal points of the normal transmission and reception of ultrasonic waves for producing the ultrasound image,
wherein the sound velocity setting processor sets an optimal sound velocity of a segment region corresponding to the one transmission focal point for sound velocity setting with use of a reception signal resulting from the transmission and reception of ultrasonic waves for forming the one transmission focal point for sound velocity setting, and
wherein the control processor causes the piezoelectric element array to form transmission focal points on the scanning line for sound velocity setting in a greater number than a number of transmission focal points on each normal scanning line in each frame for ultrasound image production, and
wherein the predetermined region is a region corresponding to a whole area of the ultrasound image to be produced.

2. A sound velocity setting method, comprising the steps of:
providing a piezoelectric element array having piezoelectric elements arranged therein, each adapted to transmit ultrasonic waves, receive ultrasonic echoes reflected by a subject, and output reception signals according to received ultrasonic waves;
providing a control processor adapted to control transmission and reception of ultrasonic waves by the piezoelectric element array;
providing a storage unit adapted to store the reception signals output by the piezoelectric element array;
providing a sound velocity setting processor adapted to divide the subject into multiple segment regions and set a sound velocity for each of the segment regions with use of the reception signals stored in the storage unit;
providing an image producing processor adapted to produce an ultrasound image by processing the reception signals output by the piezoelectric element array or the reception signals read out from the storage unit based on the sound velocity set for each of the segment regions;
at a time when a sound velocity in a subject is set by an ultrasound diagnostic apparatus,
dividing the subject into multiple segment regions;
performing transmission and reception of ultrasonic waves for forming transmission focal points for sound velocity setting in a predetermined number of frames so as to be mutually different frame by frame and to include one of plurality of scanning lines of the ultrasonic waves as a scanning line for sound velocity setting in each frame at predetermined timing such that sound velocities set for the respective segment regions in a predetermined region are all reset every predetermined number of frames, the scanning lines being formed with all of the transmission focal points for sound velocity setting;
performing transmission and reception of ultrasonic waves at predetermined timing such that scanning lines excepting the one of plurality of scanning lines in each frame are normal scanning lines of the ultrasonic waves formed of the normal transmission focal points of the transmission and reception of the ultrasonic waves for producing an ultrasound image; and
setting an optimal sound velocity of a segment region corresponding to the formed transmission focal point for sound velocity setting with use of a reception signal resulting from the transmission and reception of ultrasonic waves for forming the transmission focal point for sound velocity setting,
wherein transmission focal points on the scanning line for sound velocity setting in a greater number than a number of transmission focal points on each normal scanning line in each frame for ultrasound image production are formed, and
wherein the predetermined region is a region corresponding to a whole area of the ultrasound image to be produced.

3. A non-transitory recording medium having stored therein a program that is used by an ultrasound diagnostic apparatus to set a sound velocity of a subject and that causes a computer to implement:
a providing step of providing a piezoelectric element array having piezoelectric elements arranged therein, each adapted to transmit ultrasonic waves, receive ultrasonic echoes reflected by a subject, and output reception signals according to received ultrasonic waves;
a providing step of providing a control processor adapted to control transmission and reception of ultrasonic waves by the piezoelectric element array;
a providing step of providing a storage unit adapted to store the reception signals output by the piezoelectric element array;

a providing step of providing a sound velocity setting processor adapted to divide the subject into multiple segment regions and set a sound velocity for each of the segment regions with use of the reception signals stored in the storage unit;

a providing step of providing an image producing processor adapted to produce an ultrasound image by processing the reception signals output by the piezoelectric element array or the reception signals read out from the storage unit based on the sound velocity set for each of the segment regions, a dividing step of dividing the subject into multiple segment regions;

a transmission and reception step of performing transmission and reception of ultrasonic waves for forming transmission focal points for sound velocity setting in a predetermined number of frames so as to be mutually different frame by frame and to include one of plurality of scanning lines of ultrasonic waves as a scanning line for sound velocity setting in each frame at predetermined timing such that sound velocities set for the respective segment regions in a predetermined region are all reset every predetermined number of frames, the scanning lines being formed with all of the transmission focal points for sound velocity setting; and performing transmission and reception of ultrasonic waves at predetermined timing such that the scanning lines excepting the one of plurality of scanning lines in each frame are normal scanning lines of the ultrasonic waves formed of the transmission focal points of the normal transmission and reception of ultrasonic waves for producing an ultrasound image; and a calculation step of setting an optimal sound velocity of a segment region corresponding to the formed transmission focal point for sound velocity setting with use of a reception signal resulting from the transmission and reception of ultrasonic waves for forming the transmission focal point for sound velocity setting, wherein the transmission and reception step forms transmission focal points on the scanning line for sound velocity setting in a greater number than a number of transmission focal points on each normal scanning line in each frame for ultrasound image production, and wherein the predetermined region is a region corresponding to a whole area of the ultrasound image to be produced.

4. The ultrasound diagnostic apparatus according to claim 1, where in the sound velocity setting processor sets a sound velocity at which a contrast or a sharpness of an image is highest as the optimal sound velocity, the image being produced for each of the segment region of the scan line for sound velocity setting by the image producing processor.

5. The ultrasound diagnostic apparatus according to claim 1, wherein the sound velocity setting processor sets the optimal sound velocity of all transmission focal points for sound velocity setting.

6. A sound velocity setting method according to claim 2, wherein a sound velocity at which a contrast or sharpness of an image is highest as the optimal sound velocity, the image being produced for each of the segment region of the scan line for sound velocity setting.

7. A sound velocity setting method according to claim 2, wherein the optimal sound velocities of all transmission focal points for sound velocity setting are set.

8. The non-transitory recording medium according to claim 3, the program that causes a computer to further implement: generating the ultrasound image by processing based on the sound velocity set for each of the segment regions, wherein the stored program is configured such that a sound velocity at which a contrast or sharpness of an image is highest as the optimal sound velocity, the image being produced for each of the segment region of the scan line for sound velocity setting.

9. The non-transitory recording medium according to claim 3, wherein the optimal sound velocities of all transmission focal points for sound velocity setting are set.

* * * * *